United States Patent
Simonnet et al.

(10) Patent No.: US 6,375,960 B1
(45) Date of Patent: Apr. 23, 2002

(54) NANOEMULSION BASED ON ETHOXYLATED FATTY ETHERS OR ON ETHOXYLATED FATTY ESTERS AND ITS USES IN THE COSMETICS, DERMATOLOGICAL AND/OR OPHTHALMOLOGICAL FIELDS

(75) Inventors: Jean-Thierry Simonnet; Odile Sonneville, both of Paris; Sylvie Legret, Chatillon, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/474,074

(22) Filed: Dec. 29, 1999

(30) Foreign Application Priority Data

Dec. 29, 1998 (FR) ............................. 98 16570

(51) Int. Cl.$^7$ .......................... A61K 6/00; A61K 7/00; A61K 9/00
(52) U.S. Cl. ...................... 424/401; 424/400; 514/844; 514/845; 514/937; 514/938
(58) Field of Search ................................ 424/59, 70.23, 424/70.19, 78.03, 193.1, 400, 427, 401, 402, 450; 514/2, 785, 788, 937; 516/57, 72; 138/118.1

(56) References Cited

U.S. PATENT DOCUMENTS

| | | | |
|---|---|---|---|
| 4,083,974 A | * | 4/1978 | Turi ........................... 424/241 |
| 4,146,499 A | * | 3/1979 | Rosano ....................... 252/186 |
| 4,496,473 A | * | 1/1985 | Sanderson ............. 252/186.41 |
| 4,797,272 A | * | 1/1989 | Linn et al. ..................... 424/59 |
| 4,797,273 A | * | 1/1989 | Linn et al. ..................... 424/59 |
| 4,880,563 A | * | 11/1989 | Dahms ........................ 252/312 |
| 5,098,606 A | | 3/1992 | Nakajima et al. |
| 5,871,762 A | * | 2/1999 | Venkitaraman et al. ..... 424/402 |
| 5,925,341 A | * | 7/1999 | Cervantes et al. ........ 424/78.03 |
| 6,117,915 A | * | 9/2000 | Pereira et al. ................. 516/57 |
| 6,120,778 A | * | 9/2000 | Simonnet .................... 424/401 |

FOREIGN PATENT DOCUMENTS

| | | | | |
|---|---|---|---|---|
| EP | 0842652 A1 | * | 1/1997 | ............ A61K/7/00 |
| EP | 0852941 A1 | * | 5/1997 | ............ A61K/7/00 |
| EP | 0 842 652 A1 | | 5/1998 | |
| EP | 0 852 941 A1 | | 7/1998 | |

* cited by examiner

*Primary Examiner*—Thurman K. Page
*Assistant Examiner*—Charesse Evans
(74) *Attorney, Agent, or Firm*—Oblon, Spivak, McClelland, Maier & Neustadt, P.C.

(57) ABSTRACT

The present invention provides a nanoemulsion, that includes:

an oily phase dispersed in an aqueous phase; and at least one surfactant that is solid at a temperature of less than or equal to 45° C. and which is selected from the group including ethoxylated fatty ethers and ethoxylated fatty esters, and mixtures thereof; wherein the oily phase includes oil globules having a number-average size of less than 100 nm;

wherein the oily phase includes at least one oil having a molecular weight of greater than 400; and wherein a weight ratio of the oily phase to the surfactant ranges from 2 to 10. The invention also provides a process for making the nanoemulsion, and methods for its use. The emulsion is ideally transparent and stable on storage. It can ideally contain large amounts of oil while retaining good transparency and good cosmetic properties. The nanoemulsion is particularly useful in compositions, including topical, pharmaceutical, cosmetic, opthalmic, ophthalmologic. The composition is also particularly useful in applications to the skin, hair, scalp, mucous membranes, and eyes.

41 Claims, No Drawings

NANOEMULSION BASED ON ETHOXYLATED FATTY ETHERS OR ON ETHOXYLATED FATTY ESTERS AND ITS USES IN THE COSMETICS, DERMATOLOGICAL AND/OR OPHTHALMOLOGICAL FIELDS

BACKGROUND OF THE INVENTION

1. Field of the Invention

The present invention relates to a nanoemulsion based on a surfactant which is solid at a temperature of less than or equal to 45° C., which surfactant is chosen from ethoxylated fatty ethers and ethoxylated fatty esters, and at least one oil having a molecular weight of greater than 400, the ratio by weight of the amount of oily phase to the amount of surfactant ranging from 2 to 10.

The invention also relates to a process for the preparation of the nanoemulsion and to its uses in the cosmetics, dermatological and/or ophthahnological fields. This nanoemulsion is stable on storage and can contain large amounts of oil while retaining good transparency and while having good cosmetic properties.

2. Discussion of the Background

Nanoemulsions are oil-in-water emulsions, the oil globules of which have a very fine particle size, i.e. a number-average size of less than 100 nm. They are generally manufactured by mechanical fragmentation of an oily phase in an aqueous phase in the presence of a surfactant. In the case of nanoemulsions, the very small size of the oily globules is obtained in particular by virtue of at least one pass through a high-pressure homogenizer. The small size of the globules confers on them cosmetically advantageous properties which distinguish them from conventional emulsions: they are transparent and exhibit a novel texture. They can also carry active principles more efficiently.

Transparent microemulsions are known in the art. In contrast to nanoemulsions, microemulsions are not, strictly speaking, emulsions. Rather, microemulsions are transparent solutions of micelles swollen by oil, which oil is generally a very-short-chain oil (e.g. hexane or decane) and is solubilized by virtue of the joint presence of a significant amount of surfactants and of cosurfactants which form the micelles. The size of the swollen micelles is very small owing to the small amount of oil which they can solubilize. This very small size of the micelles is the cause of their transparency, as with nanoemulsions. However, in contrast to nanoemulsions, microemulsions are spontaneously formed by mixing the constituents, without contributing mechanical energy other than simple magnetic stirring. The major disadvantages of microemulsions are related to their necessarily high proportion of surfactants, leading to intolerance and resulting in a sticky feel during application to the skin. Furthermore, their formulation range is generally very narrow and their temperature stability very limited.

Nanoemulsions, which contain an amphiphilic lipid phase composed of phospholipids, water and oil, are known in the art. These emulsions exhibit the disadvantage of being unstable on storage at conventional storage temperatures, namely between 0 and 45° C. They lead to yellow compositions and produce rancid smells which develop after several days of storage.

Nanoemulsions stabilized by a lamellar liquid crystal coating, obtained by the combination of a hydrophilic surfactant and of a lipophilic surfactant, are also known. However, these combinations are difficult to prepare. Furthermore, the nanoemulsions obtained exhibit a waxy and film-forming feel, which is not very pleasant, for the user.

EP-A-728,460 discloses nanoemulsions based on fluid non-ionic amphiphilic lipids. However, these nanoemulsions exhibit the disadvantage of having a sticky effect during application to the skin.

The need therefore remains for nanoemulsions which have neither the disadvantages of known nanoemulsions not the disadvantages of microemulsions.

SUMMARY OF THE INVENTION

It has now been found that, surprisingly, that the use of a surfactant which is solid at a temperature of less than or equal to 45° C., which surfactant is chosen from ethoxylated fatty ethers and ethoxylated fatty esters and mixtures thereof, and of at least one oil having a molecular weight of greater than 400 (=400 grams per mole) makes it possible to obtain novel nanoemulsions exhibiting all the advantages of known nanoemulsions without their disadvantages.

Accordingly, the first embodiment of the present invention relates to a nanoemulsion that includes:

an oily phase dispersed in an aqueous phase; and at least one surfactant that is solid at a temperature of less than or equal to 45° C. and which is selected from the group including ethoxylated fatty ethers and ethoxylated fatty esters, and mixtures thereof; wherein the oily phase includes oil globules having a number-average size of less than 100 nm;

wherein the oily phase includes at least one oil having a molecular weight of greater than 400; and wherein a weight ratio of the oily phase to the surfactant ranges from 2 to 10.

Another embodiment of the present invention relates to a composition selected from the group including a topical composition, an ophthalmic vehicle, a pharmaceutical composition, dermatological composition, a cosmetic, and an opthalmological composition, and mixtures thereof, that includes the above-noted nanoemulsion.

Another embodiment of the present invention relates to a method of caring for, treating and/or making up the skin, face and/or scalp, that includes applying to the skin, face and/or scalp the above-noted nanoemulsion.

Another embodiment of the present invention relates to a method of caring for and/or treating the hair, that includes applying to the hair the above-noted nanoemulsion.

Another embodiment of the present invention relates to a method of caring for and/or moisturizing the skin, mucous membranes and/or scalp, that includes applying to the skin, mucous membranes and/or scalp the above-noted nanoemulsion.

Another embodiment of the present invention relates to a process for preparing the above-noted nanoemulsion, that includes:

mixing an aqueous phase and an oily phase with stirring at temperature ranging from 10 to 80° C. to form a mixture; and homogenizing the mixture at a pressure ranging from $6 \times 10^7$ Pa to $18 \times 10^7$ Pa.

DETAILED DESCRIPTION OF THE INVENTION

Various other objects, features and attendant advantages of the present invention will be more fully appreciated as the same becomes better understood from the following detailed description of the preferred embodiments of the invention.

The nanoemulsions according to the invention preferably have a transparent to bluish appearance. Their transparency is measured by a transmittance coefficient at 600 nm ranging from 10 to 90%, more preferably 20 to 85% or else by a turbidity preferably ranging from 60 to 600 NTU and more preferably from 70 to 300 NTU, which turbidity is measured with a Hach Model 2100 P portable turbidimeter. These ranges include all values and subranges therebetween.

The oil globules of the nanoemulsions of the invention have a number-average size of less than 100 nm, preferably ranging from 20 to 75 nm and more preferably from 40 to 60 nm. These ranges include all values and subranges therebetween. The decrease in the size of the globules makes it possible to promote the penetration of the active principles into the surface layers of the skin (carrier effect).

The surfactant which is solid at a temperature of less than or equal to 45° C. is preferably an ethoxylated fatty ether or an ethoxylated fatty ester or their mixtures. According to a more preferred embodiment of the invention, the nanoemulsion contains only one or more of a surfactant chosen from these ethers or esters, and most preferably is devoid of any surfactant other than ethoxylated fatty ethers and ethoxylated fatty esters.

The ethoxylated fatty ethers which are solid at a temperature of less than or equal to 45° C. which can be used as surfactants in the nanoemulsion according to the invention are preferably ethers formed of 1 to 100 ethylene oxide units and of at least one fatty alcohol chain having from 16 to 22 carbon atoms. The fatty chain of the ethers can be chosen in particular from behenyl, arachidyl, stearyl or cetyl units and their mixtures, such as cetearyl. Mention may be made, by way of preferred examples of ethoxylated fatty ethers, of behenyl alcohol ethers having 5, 10, 20 and 30 ethylene oxide units (CTFA names: Beheneth-5, Beheneth-10, Beheneth-20, Beheneth-30), such as the products sold under the names Nikkol BB5, BB10, BB20 and BB30 by the company Nikko, and stearyl alcohol ether having 2 ethylene oxide units (CTFA name: Steareth-2), such as the product sold under the name Brij 72 by the company ICI.

The ethoxylated fatty esters which are solid at a temperature of less than or equal to 45° C. which can be used as surfactants in the nanoemulsion according to the invention are preferably esters formed of 1 to 100 ethylene oxide units and of at least one fatty acid chain having from 16 to 22 carbon atoms. The fatty chain of the esters can be preferably chosen from stearate, behenate, arachidate or palmitate units and their mixtures. Mention may be made, by way of preferred examples of ethoxylated fatty esters, of stearic acid ester having 40 ethylene oxide units, such as the product sold under the name Myrj 52 (CTFA name: PEG-40 stearate) by the company ICI, and behenic acid ester having 8 ethylene oxide units (CTFA name: PEG-8 behenate), such as the product sold under the name Compritol HD5 ATO by the company Gattefosse.

Preferably, the amount of surfactant in the nanoemulsion of the invention can range, for example, from 0.2 to 15% by weight and more preferably from 1 to 8% by weight with respect to the total weight of the nanoemulsion. These ranges include all values and subranges therebetween.

The ratio by weight of the amount of the oily phase to the amount of surfactant ranges from 2 to 10 and preferably from 3 to 6. These ranges include all values and subranges therebetween. The term "amount of oily phase" is understood here to mean the total amount of the constituents of this phase without including the amount of surfactant.

The nanoemulsion according to the invention includes at least one oil with a molecular weight of greater than 400.

The oils with a molecular weight of greater than 400 can preferably be chosen from oils of animal or vegetable origin, mineral oils, synthetic oils and silicone oils, and their mixtures. More preferred oils of this type include, for example, isocetyl palmitate, isocetyl stearate, avocado oil or jojoba oil.

In addition, the oily phase can optionally contain other oils and in particular oils having a molecular weight of less than 400. Preferably, these oils are also chosen from oils of animal or vegetable origin, mineral oils, synthetic oils and silicone oils. Mention may be made, for example, as preferred oils with a molecular weight of less than 400, of isododecane, isohexadecane, volatile silicone oils, isopropyl myristate, isopropyl palmitate or $C_{11}$–$C_{13}$ isoparaffin.

The oily phase can optionally contain fatty substances other than the oils indicated above, such as fatty alcohols, for example stearyl, cetyl and behenyl alcohols, fatty acids, for example stearic, palmitic and behenic acids, oils of fluorinated type, waxes, gums and their mixtures.

The nanoemulsions in accordance with the invention contain an amount of oily phase preferably ranging from 2 to 40% and more preferably from 5 to 30% by weight with respect to the total weight of the nanoemulsion, the proportion of oil(s) having a molecular weight of greater than 400 preferably representing at least 40% and more preferably at least 50% by weight of the oily phase. These ranges include all values and subranges therebetween.

According to a more preferred embodiment of the invention, the nanoemulsion of the invention additionally contains one or more ionic amphiphilic lipids.

Preferred ionic amphiphilic lipids which can be used in the nanoemulsions of the invention may be chosen from the group formed by anionic amphiphilic lipids, cationic amphiphilic lipids and alkylsulphonic derivatives.

Preferably, the anionic amphiphilic lipids can be chosen from the group formed by:

the alkaline salts of dicetyl and dimyristyl phosphate;
the alkaline salts of cholesterol sulphate;
the alkaline salts of cholesterol phosphate;
iipoamino acids and their salts, such as mono- and disodium acylglutamates, such as the disodium salt of N-stearoyl-L-glutamic acid sold under the name Acylglutamate HS21 by the company Ajinomoto;
the sodium salts of phosphatidic acid;
phospholipids.

The alkylsulphonic derivatives can more particularly be chosen from the alkylsulphonic derivatives of formula (I):

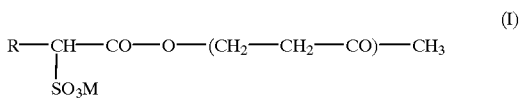

(I)

in which R represents an alkyl radical having from 16 to 22 carbon atoms, more preferably the $C_{16}H_{33}$ and $C_{18}H_{37}$ radicals, taken as a mixture or separately, and M is an alkali metal, such as sodium.

Preferably, the cationic amphiphilic lipids can be chosen from the group formed by quaternary ammonium salts, fatty amines and their salts.

The quaternary ammonium salts are, for example:

those which exhibit the following general formula (II):

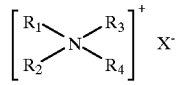

(II)

in which the $R_1$ to $R_4$ radicals, which can be identical or different, represent a linear or branched aliphatic radical having from. 1 to 30 carbon atoms or an aromatic radical, such as aryl or alkylaryl. Preferably, the aliphatic radicals can include heteroatoms, such as, in particular, oxygen, nitrogen, sulphur or halogens. Preferred aliphatic radicals include, for example, those chosen from alkyl, alkoxy, polyoxy($C_2$–$C_6$)alkylene, alkylamido, ($C_2$–$C_{22}$)alkylamido ($C_2$–$C_6$)alkyl, ($C_{12}$–$C_{22}$)alkyl acetate or hydroxyalkyl radicals having approximately from 1 to 30 carbon atoms; X is an anion chosen from the group of the halides, phosphates, acetates, lactates, ($C_2$–$C_6$)alkyl sulphates, or alkyl- or alkylarylsulphonates. Preference is given, as quaternary ammonium salts of formula (II), to, on the one hand, tetraalkylammonium chlorides, such as, for example, dialkyldimethylammonium or alkyltrimethylammonium chlorides in which the alkyl radical has approximately from 12 to 22 carbon atoms, in particular behenyltrimethylammonium, distearyldimethylammonium, cetyltrimethylammonium and benzyldimethylstearylammonium chlorides, or alternatively, on the other hand, stearamidopropyldimethyl(myristyl acetate)ammonium chloride, sold under the name "Ceraphyl 70" by the company Van Dyk.

imidazolinium quaternary ammonium salts, such as, for example, those of following formula (III):

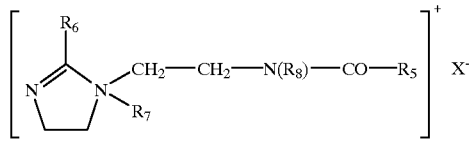

(III)

in which $R_5$ represents an alkenyl or alkyl radical having from 8 to 30 carbon atoms, preferably derived from tallow fatty acids; $R_6$ represents a hydrogen atom, an alkyl radical having from 1 to 4 carbon atoms or an alkenyl or alkyl radical having from 8 to 30 carbon atoms; $R_7$ represents an alkyl radical having from 1 to 4 carbon atoms; $R_8$ represents a hydrogen atom or an alkyl radical having from 1 to 4 carbon atoms; and X is an anion chosen from the group of the halides, phosphates, acetates, lactates, alkyl sulphates, or alkyl- or alkylarylsulphonates. $R_5$ and $R_6$ preferably denote a mixture of alkenyl or alkyl radicals having from 12 to 21 carbon atoms, preferably derived from tallow fatty acids, $R_7$ preferably denotes a methyl radical and $R_8$ preferably denotes hydrogen. Such a product is, for example, sold under the name "Rewoquat W 75" by the company Rewo. quaternary diammonium salts of formula (IV):

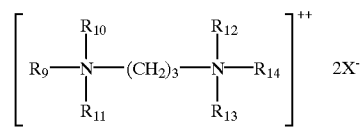

(IV)

in which $R_9$ denotes an aliphatic radical having approximately from 16 to 30 carbon atoms; $R_{10}$, $R_{11}$, $R_{12}$, $R_{13}$ and $R_{14}$ are each independently chosen from hydrogen or an alkyl radical having from 1 to 4 carbon atoms; and X is an anion chosen from the group of the halides, acetates, phosphates, nitrates and methyl sulphates.

Preferred quaternary diammonium salts include in particular propanetallowdiammonium dichloride.

According to a preferred embodiment of the invention, a lipoamino acid is used as ionic amphiphilic lipid.

Preferably, the ionic amphiphilic lipids can be introduced into one or other phase of the nanoemulsion. When they are present in the nanoemulsion of the invention, they can be used in concentrations preferably ranging from 0.01 to 5% by weight and more particularly from 0.25 to 1% by weight with respect to the total weight of the nanoemulsion. These ranges include all values and subranges therebetween.

The emulsions in accordance with the present invention can optionally contain additives for improving the transparency of the formulation. These additives are preferably chosen from the group formed by:

lower alcohols having from 1 to 8 carbon atoms and more particularly from 2 to 6 carbon atoms, such as ethanol;

glycols, such as glycerol, propylene glycol, 1,3-butylene glycol, dipropylene glycol, pentylene glycol, isoprene glycol and polyethylene glycols having from 4 to 16 and preferably from 8 to 12 ethylene oxide units;

sugars, such as glucose, fructose, maltose, lactose or sucrose.

These additives can preferably be used as a mixture. When they are present in the nanoemulsion of the invention, they can be used at concentrations preferably ranging from 0.01 to 30% by weight, more preferably from 0.3 to 25%, and most preferably from 5 to 20% by weight with respect to the total weight of the nanoemulsion. The amount of alcohol(s) and/or of sugar(s) preferably ranges from 5 to 20% by weight and more preferably from 10 to 15% by weight with respect to the total weight of the nanoemulsion and the amount of glycol(s) preferably ranges from 5 to 15% by weight with respect to the total weight of the nanoemulsion. These ranges include all values and subranges therebetween.

To obtain preservative-free emulsions, it is preferred to use the alcohols as defined above at concentrations greater than or equal to 15% by weight with respect to the total weight of the nanoemulsion.

The nanoemulsions defined above can be used in any field where this type of composition is useful. They can are particularly useful in compositions for topical use and, most particularly, in particular cosmetic or dermatological compositions. They can also be used as ophthalmic vehicles. In addition, they are especially useful in the pharmaceutical field, e.g. a pharmaceutical composition which can be administered orally, parenterally or transcutaneously.

A preferred embodiment of the invention is therefore a composition for topical use, characterized in that it contains a nanoemulsion as defined above.

Preferably, a composition for topical or pharmaceutical use contains a physiologically acceptable medium, i.e. one that is compatible with the skin, mucous membranes, scalp, eyes and/or hair.

Another preferred embodiment of the invention is an ophthalmic vehicle, characterized in that it contains a nanoemulsion as defined above.

Another preferred embodiment of the invention is a pharmaceutical composition, characterized in that it contains a nanoemulsion as defined above.

Preferably, the nanoemulsions of the invention may optionally contain water-soluble or fat-soluble active principles having a cosmetic, dermatological or ophthalmic activity. The fat-soluble active principles are in the oily globules of the emulsion, whereas the water-soluble active principles are in the aqueous phase of the emulsion. Preferred examples of active principles include vitamins, such as vitamin E, and their derivatives and in particular their esters, provitamins, such as panthenol, humectants and sun screen agents.

Preferable ophthalmic active principles include, for example, antiglaucoma agents, such as betaxolol; antibiotics, such as acyclovir; antiallergics; anti-inflammatory agents, such as ibuprofen and its salts, diclofenac and its salts, or indomethacin; or antiviral agents.

The nanoemulsions in accordance with the invention can be provided in the form of a lotion, serum, cream, milk or toilet water and can contain adjuvants commonly used in the cosmetics, dermatological and ophthalmic fields, such as, for example, gelling agents, preservatives, antioxidants and fragrances. They can also be provided in the form of an eye lotion, in particular for ophthalmological applications.

Preferred gelling agents which can be used include cellulose derivatives, algal derivatives, natural gums and synthetic. polymers, such as polymers and copolymers of carboxyvinyl acids, for example those sold under the name Carbopol by the company Goodrich.

Another preferred embodiment of the invention is a process for the preparation of a nanoemulsion as defined above, this process including the mixing of the aqueous phase and the oily phase with vigorous stirring at a temperature ranging from 10 to 80° C. and then a homogenization of the mixture at a pressure preferably ranging from $6 \times 10^7$ Pa to $18 \times 10^7$ Pa (high-pressure homogenization). The shearing (e.g. mixing or stirring) preferably ranges from $2 \times 10^6$ s$^{-1}$ to $5 \times 10^8$ s$^{-1}$ and more preferably from $1 \times 10^8$ s$^{-1}$ to $3 \times 10^8$ s$^{-1}$ (s-1 signifies second$^{-1}$). These ranges include all values and subranges therebetween.

The nanoemulsion of the invention can be most preferably used, for example, for caring for, treating or making up the skin, face and/or scalp.

Another preferred embodiment of the invention is therefore the cosmetic use of the nanoemulsion as defined above for caring for, treating and/or making up the skin, face and/or scalp.

Preferably, the nanoemulsion of the invention can also be used for caring for and/or treating the hair. It makes it possible to obtain a deposit of oil on the hair, which renders the latter glossier and more resistant to styling, without, however, making it lank. It also makes it possible, as a pretreatment, to improve the effects of dyeing or permanent waving.

Another preferred embodiment of the invention is therefore the cosmetic use of the nanoemulsion as defined above for caring for and/or treating the hair.

The nanoemulsion according to the invention is excellent for moisturizing the skin, mucous membranes and/or scalp and is particularly suited to the treatment of dry skin.

Another preferred embodiment of the invention is therefore a cosmetic process for caring for and/or moisturizing the skin, mucous membranes and/or scalp, characterized in that a nanoemulsion as defined above is applied to the skin, mucous membranes and/or scalp.

Another preferred embodiment relates to the use of the nanoemulsion according to the invention in the manufacture of a dermatological composition intended for the treatment of dry skin.

Another preferred embodiment relates to the use of the nanoemulsion according to the invention in the manufacture of an ophthalmological composition.

EXAMPLES

Having generally described the invention, a further understanding can be obtained by reference to certain specific examples which are provided herein for purposes of illustration only and are not intended to be limiting unless otherwise specified. The amounts shown are as % by weight.

Example 1

Fluid Make-up Remover

| Oily phase: | |
|---|---|
| Brij 72 (Company ICI) | 4.5% |
| Disodium salt of N-stearoyl-L-glutamic acid (Acylglutamate HS21 from the company Ajinomoto) | 0.5% |
| Isocetyl stearate (M.W. = 508) | 10% |
| Isopropyl myristate (M.W. = 270) | 5% |
| Aqueous phase: | |
| Glycerol | 5% |
| Dipropylene glycol | 10% |
| Water | 65% |

A transparent nanoemulsion is obtained, the size of the globules of which is 47 nm and the turbidity of which is 222 NTU.

Example 2

Scented Water for the Body

| Oily phase: | |
|---|---|
| Nikkol BB10 (Company Nikko) | 4.5% |
| Disodium salt of N-stearoyl-L-glutamic acid (Acylglutamate HS21 from the company Ajinomoto) | 0.5% |
| Soybean oil (M.W. of the order of 900) | 8.5% |
| Volatile silicone oil (M.W. 106) | 3% |
| Fragrance | 3% |
| Vitamin E acetate | 0.5% |
| Ethanol | 12.5% |
| Aqueous phase: | |
| Glycerol | 5% |
| Water   q.s. for | 100% |

A transparent nanoemulsion is obtained, the size of the globules of which is 42 nm and the turbidity of which is 149 NTU.

Example 3

Hair Care

| Oily phase: | |
| --- | --- |
| Compritol HD5 ATO (Company Gattefosse) | 4% |
| Behenyltrimethylammonium chloride | 1% |
| Avocado oil (M.W. of the order of 900) | 15% |
| Ethanol | 20% |
| Aqueous phase: | |
| Glycerol | 5% |
| Water   q.s. for | 100% |

A transparent nanoemulsion is obtained, the size of the globules of which is 55 nm and the turbidity of which is 230 NTU.

Obviously, numerous modifications and variations of the present invention are possible in light of the above teachings. It is therefore to be understood that within the scope of the appended claims, the invention may be practiced otherwise than as specifically described herein.

This application is based on French Patent Application 98 16570, filed Dec. 29, 1998, the entire contents of which are hereby incorporated by reference.

What is claimed is:

1. A nanoemulsion, comprising:
   an oily phase dispersed in an aqueous phase; and
   at least one surfactant that is solid at a temperature of less than or equal to 45° C. and which is selected from the group consisting of (a), (b), and (c):
   (a) at least one ether formed from 1 to 100 ethylene oxide units and at least one fatty alcohol chain having from 16 to 22 carbon atoms, and
   (b) at least one ester formed from 1 to 100 ethylene oxide units and at least one fatty acid chain having from 16 to 22 carbon atoms, and
   (c) mixtures thereof;
      wherein said oily phase comprises oil globules having a number-average size of from 20 to less than 100 nm;
      wherein said oily phase comprises at least one oil having a molecular weight of greater than 400; and
      wherein a weight ratio of said oily phase to said surfactant ranges from 2 to 10; and
      wherein said oily phase is present in an amount of 10–40% by weight, based on the total weight of said nanoemulsion.

2. The nanoemulsion according to claim 1, further comprising a turbidity ranging from 60 to 600 NTU.

3. The nanoemulsion according claim 1, wherein said surfactant is present in an amount ranging from 0.2 to 15% by weight based on the total weight of the nanoemulsion.

4. The nanoemulsion according claim 1, wherein said weight ratio of said oily phase to said surfactant ranges from 3 to 6.

5. The nanoemulsion according to claim 1, wherein said oil globules have an number-average size ranging from 20 to 75 nm.

6. The nanoemulsion according to claim 1, wherein said ethoxylated fatty ethers and ethoxylated fatty esters are selected from the group consisting of:
   behenyl alcohol ether having any of 5, 10, 20 or 30 ethylene oxide units,
   stearyl alcohol ether having 2 ethylene oxide units,
   behenic acid ester having 8 ethylene oxide units, and
   stearic acid ester having 40 ethylene oxide units, and mixtures thereof.

7. The nanoemulsion according to claim 1, wherein said oil is selected from the group consisting of oils of animal or vegetable origin, mineral oils, synthetic oils and silicone oils, and mixtures thereof.

8. The nanoemulsion according to claim 1, wherein said oily phase further comprises at least one oil having a molecular weight of less than 400.

9. The nanoemulsion according to claim 1, wherein said oil is present in said oily phase in an amount of at least 40% by weight based on the total weight of the oily phase.

10. The nanoemulsion according to claim 1, further comprising at least one ionic amphiphilic lipid selected from the group consisting of anionic amphiphilic lipids, cationic amphiphilic lipids and alkylsulphonic derivatives.

11. The nanoemulsion according to claim 10, wherein said anionic amphiphilic lipids, cationic amphiphilic lipids and alkylsulphonic derivatives are selected from the group consisting of:
   alkaline salts of dicetyl and dimyristyl phosphate;
   alkaline salts of cholesterol sulphate;
   alkaline salts of cholesterol phosphate;
   salts of lipoamino acids;
   sodium salts of phosphatidic acid;
   phospholipids;
   alkylsulphonic derivatives of formula (I):

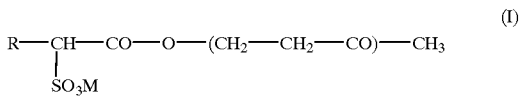

in which R represents $C_{16}$–$C_{22}$ alkyl radicals, taken as a mixture or separately, and M is an alkali metal;
   quaternary ammonium salts;
   fatty amines and salts thereof; and mixtures thereof.

12. The nanoemulsion according to claim 10, wherein said ionic amphiphilic lipid is present in an amount ranging from 0.01 to 5% by weight based on the total weight of the nanoemulsion.

13. The nanoemulsion according to claim 1, further comprising a transparency-improving additive selected from the group consisting of lower alcohols, glycols, sugars and mixtures thereof.

14. The nanoemulsion according to claim 13, wherein said additive is present in a concentration ranging from 5 to 20% by weight based on the total weight of the nanoemulsion.

15. The nanoemulsion according to claim 1, further comprising a cosmetic, dermatological or ophthalmological active principle.

16. A composition selected from the group consisting of a topical composition, an ophthalmic vehicle, a pharmaceutical composition, dermatological composition, a cosmetic, and an opthalmological composition, and mixtures thereof, comprising the nanoemulsion as claimed in claim 1.

17. A method of caring for, treating and/or making up the skin, face and/or scalp, comprising applying to the skin, face and/or scalp the nanoemulsion as claimed in claim 1.

18. A method of caring for and/or treating the hair, comprising applying to the hair the nanoemulsion as claimed in claim 1.

19. A method of caring for and/or moisturizing the skin, mucous membranes and/or scalp, comprising applying to the skin, mucous membranes and/or scalp the nanoemulsion as claimed in claim 1.

20. A process for preparing the nanoemulsion as claimed in claim 1, comprising:

mixing an aqueous phase and an oily phase with stirring at temperature ranging from 10 to 80° C. to form a mixture; and homogenizing the mixture at a pressure ranging from $6\times10^7$ Pa to $18\times10^7$ Pa to produce the nanoemulsion as claimed in claim 1.

21. The process according to claim 20, wherein a shearing is carried out at a rate ranging from $2\times10^6$ s$^{-1}$ to $5\times10^8$ s$^{-1}$.

22. The nanoemulsion according to claim 1, wherein said oily phase is present in an amount of 15–40% by weight, based on the weight of said nanoemulsion.

23. The nanoemulsion according to claim 1, wherein said oily phase is present in an amount of 15–30% by weight, based on the weight of said nanoemulsion.

24. The nanoemulsion according to claim 1, wherein said oily phase is present in an amount of 15% by weight, based on the weight of said nanoemulsion.

25. The nanoemulsion according to claim 1, wherein said oily phase is present in an amount of 40% by weight, based on the weight of said nanoemulsion.

26. The nanoemulsion according to claim 1, wherein said nanoemulsion further comprises greater than or equal to 15% by weight of at least one alcohol, based on the total weight of the nanoemulsion.

27. The nanoemulsion according to claim 26, which does not contain a preservative.

28. The nanoemulsion according to claim 1, further comprising a transparency-improving additive selected from the group consisting of lower alcohols, glycols and mixtures thereof.

29. The nanoemulsion according to claim 28, wherein said additive is present in a concentration ranging from 5 to 20% by weight based on the total weight of the nanoemulsion.

30. The nanoemulsion according to claim 1, wherein said surfactant is at least one ethoxylated fatty ether.

31. The nanoemulsion according to claim 30, further comprising a transparency-improving additive selected from the group consisting of lower alcohols, glycols and mixtures thereof.

32. The nanoemulsion according to claim 30, wherein said additive is present in a concentration ranging from 5 to 20% by weight based on the total weight of the nanoemulsion.

33. The nanoemulsion according to claim 1, wherein said surfactant is at least one ethoxylated fatty ester.

34. The nanoemulsion according to claim 33, further comprising a transparency-improving additive selected from the group consisting of lower alcohols, glycols and mixtures thereof.

35. The nanoemulsion according to claim 33, wherein said additive is present in a concentration ranging from 5 to 20% by weight based on the total weight of the nanoemulsion.

36. The nanoemulsion according to claim 1, wherein said surfactant is a stearyl alcohol ether having 2 ethylene oxide units;

wherein said oil globules have a number-average size of 47 nm; and wherein said oil having a molecular weight of greater than 400 is isocetyl stearate.

37. The nanoemulsion according to claim 1, which comprises:

4.5% by weight of stearyl alcohol ether having 2 ethylene oxide units;

0.5% by weight of disodium salt of N-stearoyl-L-glutamic acid;

10% by weight of isocetyl stearate;

5% by weight of isopropyl myristate;

5% by weight of glycerol;

10% by weight of dipropylene glycol; and

65% by weight of water.

38. The nanoemulsion according to claim 1, wherein said surfactant is a behenyl alcohol ether having 10 ethylene oxide units;

wherein said oil globules have a number-average size of 42 nm; and wherein said oil having a molecular weight of greater than 400 is soybean oil.

39. The nanoemulsion according to claim 1, which comprises:

4.5% by weight of behenyl alcohol ether having 10 ethylene oxide units;

0.5% by weight of disodium salt of N-stearoyl-L-glutamic acid;

8.5% by weight of soybean oil;

3% by weight of volatile silicone oil;

3% by weight of fragrance;

0.5% by weight of vitamin E acetate;

12.5% by weight of ethanol;

5% by weight of glycerol; and q.s. for 100% by weight of water.

40. The nanoemulsion according to claim 1, wherein said surfactant is a behenic acid ester having 8 ethylene oxide units;

wherein said oil globules have a number-average size of 55 nm; and wherein said oil having a molecular weight of greater than 400 is avocado oil.

41. The nanoemulsion according to claim 1, which comprises:

4% by weight of behenic acid ester having 8 ethylene oxide units;

1% by weight of behenyltrimethylammonium chloride;

15% by weight of avocado oil;

20% by weight of ethanol;

5% by weight of glycerol; and q.s. for 100% by weight of water.

* * * * *